United States Patent [19]

Wodlinger

[11] Patent Number: 5,706,823
[45] Date of Patent: Jan. 13, 1998

[54] ELECTROPHYSIOLOGY FILTERING SYSTEM

[75] Inventor: Harold Max Wodlinger, Thornhill, Canada

[73] Assignee: Quinton Instrument Company, Bothell, Wash.

[21] Appl. No.: 695,484

[22] Filed: Aug. 12, 1996

Related U.S. Application Data

[60] Provisional application No. 60/002,535, Aug. 18, 1995.

[51] Int. Cl.⁶ .......................... A61B 5/0402; A61B 17/39
[52] U.S. Cl. ............................ 128/696; 128/710; 606/34; 606/40
[58] Field of Search ...................... 606/32, 34, 40, 606/41, 49; 607/98, 99, 122; 128/642, 696, 710

[56] References Cited

U.S. PATENT DOCUMENTS

| | | | |
|---|---|---|---|
| 3,789,834 | 2/1974 | Duroux | 128/2.1 Z |
| 3,960,141 | 6/1976 | Bolduc | 128/2.06 E |
| 4,161,945 | 7/1979 | Grossman | 128/696 |
| 4,240,445 | 12/1980 | Iskander et al. | 128/804 |
| 4,245,649 | 1/1981 | Schmidt-Andersen | 128/696 |
| 4,291,707 | 9/1981 | Heilman et al. | 128/784 |
| 4,328,809 | 5/1982 | Hirschowitz et al. | 128/653 |
| 4,346,716 | 8/1982 | Carr | 128/653 |
| 4,409,993 | 10/1983 | Furihata | 128/784 |
| 4,416,276 | 11/1983 | Newton et al. | 128/303.13 |
| 4,432,369 | 2/1984 | Halvorsen | 128/653 |
| 4,537,200 | 8/1985 | Widrow | 128/696 |
| 4,630,611 | 12/1986 | King | 128/642 |
| 4,641,649 | 2/1987 | Walinsky et al. | 128/303.1 |
| 4,660,571 | 4/1987 | Hess et al. | 128/784 |
| 4,785,815 | 11/1988 | Cohen | 128/642 |
| 4,805,621 | 2/1989 | Heinze et al. | 128/419 PG |
| 4,869,248 | 9/1989 | Narula | 128/303.13 |
| 4,896,671 | 1/1990 | Cunningham et al. | 128/642 |
| 4,922,912 | 5/1990 | Watanabe | 128/642 |
| 4,945,912 | 8/1990 | Langberg | 128/642 |
| 4,955,382 | 9/1990 | Franz et al. | 128/642 |
| 4,966,597 | 10/1990 | Cosman | 606/50 |
| 5,056,517 | 10/1991 | Fenici | 128/419 P |
| 5,156,151 | 10/1992 | Imran | 128/642 |
| 5,172,699 | 12/1992 | Svenson et al. | 128/705 |
| 5,228,442 | 7/1993 | Imran | 128/642 |
| 5,239,999 | 8/1993 | Imran | 128/642 |
| 5,259,387 | 11/1993 | dePinto | 128/696 |
| 5,281,215 | 1/1994 | Milder | 606/20 |
| 5,295,484 | 3/1994 | Marcus et al. | 128/660.03 |
| 5,311,873 | 5/1994 | Savard et al. | 128/696 |
| 5,318,036 | 6/1994 | Arand et al. | 128/696 |
| 5,341,807 | 8/1994 | Nardella | 128/642 |
| 5,357,956 | 10/1994 | Nardella | 128/642 |
| 5,370,644 | 12/1994 | Langberg | 606/33 |
| 5,391,199 | 2/1995 | Ben-Haim | 607/122 |
| 5,398,683 | 3/1995 | Edwards et al. | 128/642 |
| 5,402,795 | 4/1995 | Reichl | 128/696 |
| 5,405,376 | 4/1995 | Mulier et al. | 607/127 |

*Primary Examiner*—Lee S. Cohen
*Attorney, Agent, or Firm*—Montgomery W. Smith; Richard D. Allison

[57] ABSTRACT

A versatile electrophysiology system including an amplification system, an ablation machine, a filter box, a display monitor and a chart recorder as well as an optional data management and analysis system wherein the amplification system receives endocardial signals from an ablation catheter during both the electrophysiology study and the ablation procedure and wherein the amplification system, ablation machine and ablation catheter are interconnected with the filter box such that the endocardial signals and the high energy ablation signal pass therethrough and are filtered thereby.

32 Claims, 3 Drawing Sheets

ELECTROPHYSIOLOGY FILTERING SYSTEM

This application claims the benefit of U.S. Provisional Application No. 60/002,535, filed Aug. 18, 1995.

FIELD OF THE INVENTION

This invention relates generally to an electrophysiology signal filtering system. More specifically, the present invention relates to an electrophysiology system for continuous monitoring of the electrical signal from the endocardium of the patient during an electrophysiology study as well as during the application of ablation energy to the patient. Also, the present invention relates to an automatic filtering system for filtering the noise generated by the ablation machine during the electrophysiology study as well as providing a higher impedance coupling to the endocardial signal generated by the patient during the ablation procedure. One form of the present invention includes a filter box operatively connected between an amplification system, an ablation machine and an ablation catheter such that the filter box includes a passive filter with low impedance capacitors and high impedance inductors at the frequencies of the ablation signals to enable the amplification system to receive intracardiac signals during the ablation procedure.

BACKGROUND OF THE INVENTION

In order to more fully appreciate the present invention, it is important to understand the basic principles of electrophysiology studies and ablation procedures and the configuration of the presently available electrophysiology systems. The electrophysiology study is used to assist the physician in evaluating a broad spectrum of cardiac arrhythmias and malfunctions in the electrical pathways of the heart. The basic electrophysiology study involves the recording and pacing of electrical signals within localized areas of the heart. Pacing is used to introduce artificially premature electrical impulses. The catheters used in electrophysiology studies generally consist of insulated wires having a distal end with electrodes thereon. The electrodes are exposed to the intracardiac surface of the patient. The proximal end of the catheter includes various plugs or connectors thereon which correspond to certain electrodes at the distal end or ablation pole of the catheter.

The recording of the electrical activity from an electrode catheter placed in the heart of the patient is referred to as an intracardiac electrogram. An important difference between a body surface ECG and an intracardiac electrogram is that the body surface ECG represents a summation of the entire electrical activity of the heart of the patient while the intracardiac electrogram represents the electrical activity of a localized area of interest.

Current electrophysiology systems typically perform two types of pacing or programmed stimulation for use in electrophysiology studies. The first type of pacing is known as incremental or burst pacing where a train of fixed pulses is generated and applied to the endocardium of the patient at a fixed cycle length. This type of pacing may last for a few beats or for several minutes. The other primary type of pacing is known as extra-stimulus pacing where one or more premature impulses are produced at their own specific coupling interval. The electrophysiology study allows the physician to move the distal end of the electrode catheter to various locations in the heart of the patient and also to select various electrode pairs to monitor the electrical conduction characteristics of very specific areas of the heart of the patient to determine whether or not certain areas of the endocardium are diseased or damaged.

The basic equipment used in electrophysiology studies and ablation procedures consist of a programmable stimulator, a multichannel lead switching box, an ablation machine, one or more display monitors, a signal amplification system, a printer and ablation catheters. The programmable stimulator is a specialized pacing unit built particularly for electrophysiology studies. The stimulator has the capability to introduce complex sequences of paced beats to within an accuracy of one millisecond to the endocardium of the patient and may also provide pacing which is synchronous with the intrinsic heart rhythm of the patient or perform simultaneous pacing of multiple intracardiac sites.

The multichannel lead switching box or junction box may be a separate component or contained within an amplification system. The switching box allows the laboratory personnel to control the connections from the electrode catheters to various recording and pacing devices. The switching box includes multiple switches to allow for the sorting of multiple electrode pairs from multiple catheters for recording and pacing the intracardiac areas of interest.

The ablation machines are used during the electrophysiology procedure to generate physical energy such as direct current countershock, modified low-energy DC, radio frequency, laser, microwave, thermal or other energy sources to generate a signal to ablate the selected portion of the endocardium in response to the results of the electrophysiology study. A DC ablation machine may consist of a modified defibrillator which delivers the energy signal through the catheter to the endocardium of the patient. For example, the DC ablation machine may be used to deliver an energy signal of approximately 3 to 5 watt-seconds per kilogram to the desired location along the bundle of His in the endocardium of the patient to ablate the portion of the bundle of His which is adjacent to the catheter. These machines may be used to provide high energy shocks typically in the range of approximately 30 or 35 joules. The more typical RF ablation machine involves the application of a 500 kHz signal for between about 30 and 60 seconds at a power level of between about 20 to 40 watts. Various RF ablation machines are commercially available and provide certain advantages for certain types of procedures and may include an adjustable electrical energy source which is automatically adjusted in response to the temperature sensed at the distal tip of the ablation catheter.

One difficulty with currently available electrophysiology systems is that the ablation machine and the monitoring system must be alternately connected to the ablating pole of the ablation catheter through a switch box to alternately connect the catheter to a sensing amplifier to monitor the endocardial signal in a first setting and to the ablation machine to apply ablation signals in a second setting. Therefore, the physician is unable to monitor the endocardial signal during the ablation procedure and must manually switch the switch box back to the monitoring position to monitor the intracardiac signals of the patient.

There are two characteristics of electrophysiology systems which inhibit or prevent simultaneous monitoring of the endocardial signal during the delivery of ablation energy. The first characteristic of these systems is that large amounts of electrical noise are generated by ablation machines in addition to the high energy ablation signal. The electrical noise generated by the ablation machine is generally in the same frequency band as the signals generated by the endocardium of the patient and therefore is not removed by the amplification system in current electrophysiology systems. The second characteristic of electrophysiology systems is that the ablation machine delivers the ablation energy through low impedance couplings in order to ensure that the majority of ablation energy reaches the target area of the heart. The low impedance coupling typically overpowers or shorts out the electrical signal generated by the endocardium. Therefore, it is necessary to switch the switchbox between first and second settings during an ablation procedure to monitor the endocardial signals of the patient and it is not possible to monitor the endocardial signal during the application of the ablation energy to the patient. With the currently available electrophysiology systems, it is necessary for the physician to discontinue the application of ablation energy from the ablation machine in order for the physician to verify the need to discontinue, apply further ablation energy or move the catheter to a new location in the endocardium of the patient.

OBJECTS AND SUMMARY OF THE INVENTION

An object of the present invention is to provide a versatile electrophysiology system including a complete electrophysiology system consisting of an ablation machine, a data management and analysis system, a real time display monitor, an electrical signal amplification system and a chart recorder while eliminating the prior need for a switch box.

A further object of the present invention is to provide an electrophysiology system having an automatic filtering mechanism which allows for the monitoring of the signals from the endocardium during the electrophysiology study and the ablation procedure through the same pole of an ablation catheter.

It is another object of the present invention to provide a filter box which blocks the interfering in band noise generated by the ablation machine while allowing the high energy ablation signal to pass without restriction while providing a high impedance to the endocardial signal to enable the endocardial signal to be monitored by the amplification system without attenuation. The amplification system then receives a signal which is a combination of a filtered ablation signal and the endocardial signal. The amplification system then filters out the ablation signal. Yet another object of the present invention is to provide an electrophysiology system which considerably simplifies setup and preprocedure requirements as well as setup changes during an ongoing signal acquisition study and during the ablation procedure by allowing the entire system to be setup prior to the procedure without the need to adjust or switch components of the system for use in either the electrophysiology study or the ablation procedure.

Another object of the present invention is to provide an electrophysiology system which does not require manual switching between the monitoring and acquisition portion of the system and the ablation machine.

These and other objects of the present invention are realized in a presently preferred embodiment described in more detail below. The presently preferred embodiment is disclosed by way of example and not by way of limitation and includes an electrophysiology system having an ablation machine, an ablation catheter, a filter box and an integrated electrical signal amplification system for use in electrophysiology studies and ablation procedures. The filter box is provided as an interface between electrical signals received from a patient through sensors such as intracardiac or ablation catheters and the ablation machine. The amplification system is electrically connected to a real time display monitor, chart recorder, and/or a computer processing and analysis unit. The amplification system uses digital technology to amplify and condition electrical signals from a patient's heart and download analog formatted signals to a computer processing unit, a real time display monitor and/or a chart recorder.

The filter box is electrically connected between the ablation catheter, the ablation machine and the amplification system to eliminate the need for the physician to manually switch between the ablation machine and the amplification and monitoring components of the system. The electrophysiology system of the present invention has a unique advantage over prior art electrophysiology systems in that it ensures the possibility of uninterrupted endocardial signals during the electrophysiology study and the ablation procedure. This feature allows the system of the present invention to be used to provide information about the endocardial signals of the patient during an ablation procedure, which is the most critical time for the physician to receive such signals.

The filter box of the present invention includes a novel electrical hardware design that improves signal conditioning performance and provides a mixed signal to the amplification system which includes the filtered ablation signal and the endocardial signal. The amplification system then removes the filtered ablation signal and amplifies the endocardial signal for use by the analysis and monitoring portions of the electrophysiology system. Specifically, the present invention includes capacitors which offer a very low impedance to the ablation energy while inductors offer a high impedance to ground at ablation frequencies. The capacitors preferably have an impedance which is preferably less than one ohm and the inductors have an impedance which is preferably greater than 3000 ohms at 500 kHz. A filter pole of approximately 5000 to 10000 Hz serves to block all in band noise generated by the ablation machine at the ablation side of the filter box and to block the endocardial signal on the patient side of the filter box to allow it to be amplified and monitored by the amplification system. The filtered ablation signal is then processed by low pass filters in the amplification system to leave only the endocardial signal for use by the amplification system, analysis system and monitors.

The amplification system of the present invention can also be adapted for use in hemodynamic studies in conjunction with electrophysiology studies due to its ability to receive and process various signals including pressure inputs.

The data management and analysis system of the present invention preferably provides up to 32 channels of real time analog wave form acquisition, scrolling or panning displays, storage and statistics. Once storage has been conducted, playback, markers, annotations, analysis and hard copy printouts may be performed. The major components of the data management and analysis system include a micro computer, keyboard, mouse, laser printer and may be interconnected with a separate fluoroscopic viewing system to provide the physician with a means for visually identifying the location of the catheters.

The foregoing objects and briefly described features of the electrophysiology system of the present invention are described with respect to the preferred forms of the present invention as set forth in detail below.

BRIEF DESCRIPTION OF THE DRAWINGS

Other features and advantages of the present invention will become more apparent with reference to the following description of the preferred embodiment and the accompanying drawings in which similar elements are represented by like numerals throughout, and in which.

DETAILED DESCRIPTION OF THE PREFERRED EMBODIMENTS

Figure 1:
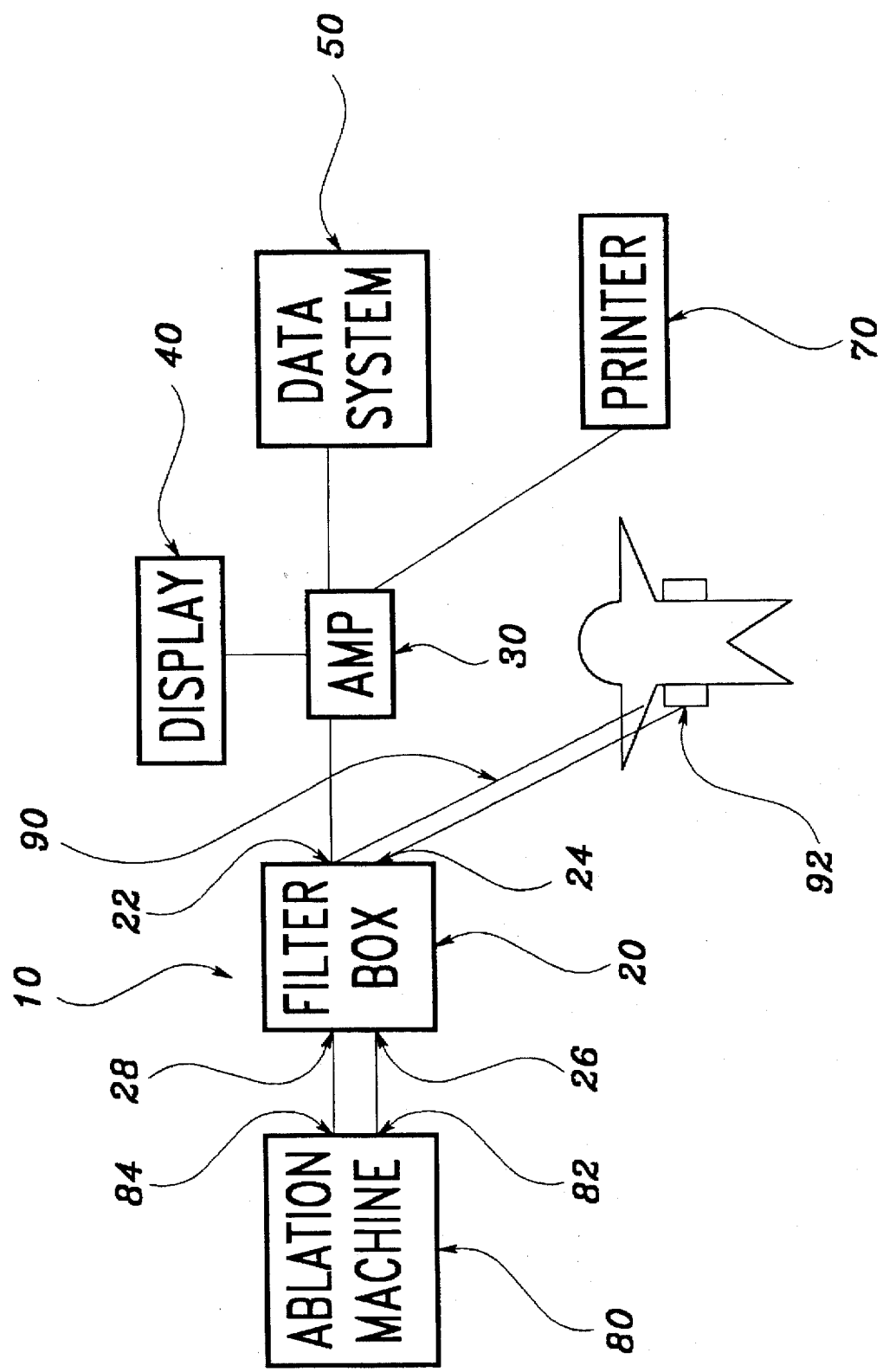
FIG. 1 is a diagrammatic view of a preferred embodiment of an electrophysiology system formed in accordance with the principles of the present invention.
Figure 2:
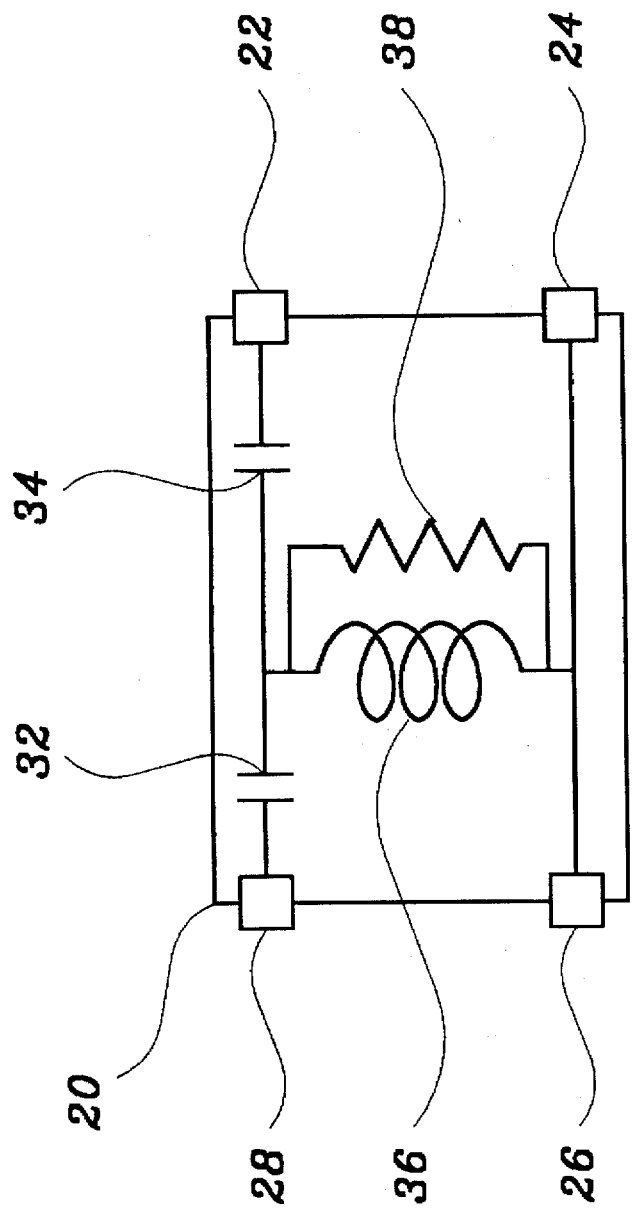
FIG. 2 is a diagrammatic view of the filter box of the preferred embodiment of the present invention.

FIGS. 1 and 2 are provided as exemplary drawings to illustrate the preferred embodiment of the versatile electrophysiology system made in accordance with the principals of the present invention. As described more fully below and shown in the drawings, the electrophysiology system 10 may include a separate filter box referred to generally by the reference numeral 20, an amplification system referred to generally by the reference numeral 30, a real time display monitor referred to generally by the reference numeral 40, a data management and analysis system referred to generally by the reference numeral 50, a chart recorder or printer referred to generally by the reference numeral 70, an ablation machine referred to generally by the reference numeral 80 and an ablation electrode or catheter 90. Alternately, as also described below, the electrophysiology system may be configured to include a modified filter box 25 which is integral with and shielded from the amplification system 30 and/or an optional interface unit (not shown).

As shown in FIG. 1, the preferred form of the electrophysiology system 10 facilitates the simplified setup and operation of an electrophysiology study and ablation procedure by allowing the entire system 10 to be setup prior to the study and procedure and without having to adjust switches when changing from the electrophysiology study to the ablation procedure.

More specifically, as shown in FIG. 1, the electrophysiology system 10 of the present embodiment includes a standard ablation catheter 90 which includes a distal end that is positioned in the heart of the patient using fluoroscopy and/or electrical signal sensing. The proximal end of the ablation catheter 90 is connected to the Filter Out terminal 22 on the patient side of the filter box 20. The signal to and from the ablation electrode 90 is connected in parallel with the input to the amplification system 30 to the filter box 20 so that the amplification system 30 is connected therewith. As is conventional in electrophysiology studies and ablation procedures, the patient is positioned on a conductive ground pad 92 which allows the electrical energy to pass through the patient and back to the electrophysiology system 10. In the present invention, the ground pad 92 is connected to the patient ground terminal 24 on the patient side of the filter box 20 which is connected to the machine ground terminal 26 on the ablation side of the filter box 20 to connect with the ground 82 from the ablation machine 80. The ablation machine 80 is connected to the opposite side of the filter box 20 so that the active terminal 84 of the ablation machine is connected to the filter In terminal 28 on the ablation machine side of the filter box 20 and the machine ground terminal 26 which is also located on the ablation side of the filter box 20 allows the ground 82 from the ablation machine 80 to be connected to the filter box 20 and the ground pad 92.

Figure 3:
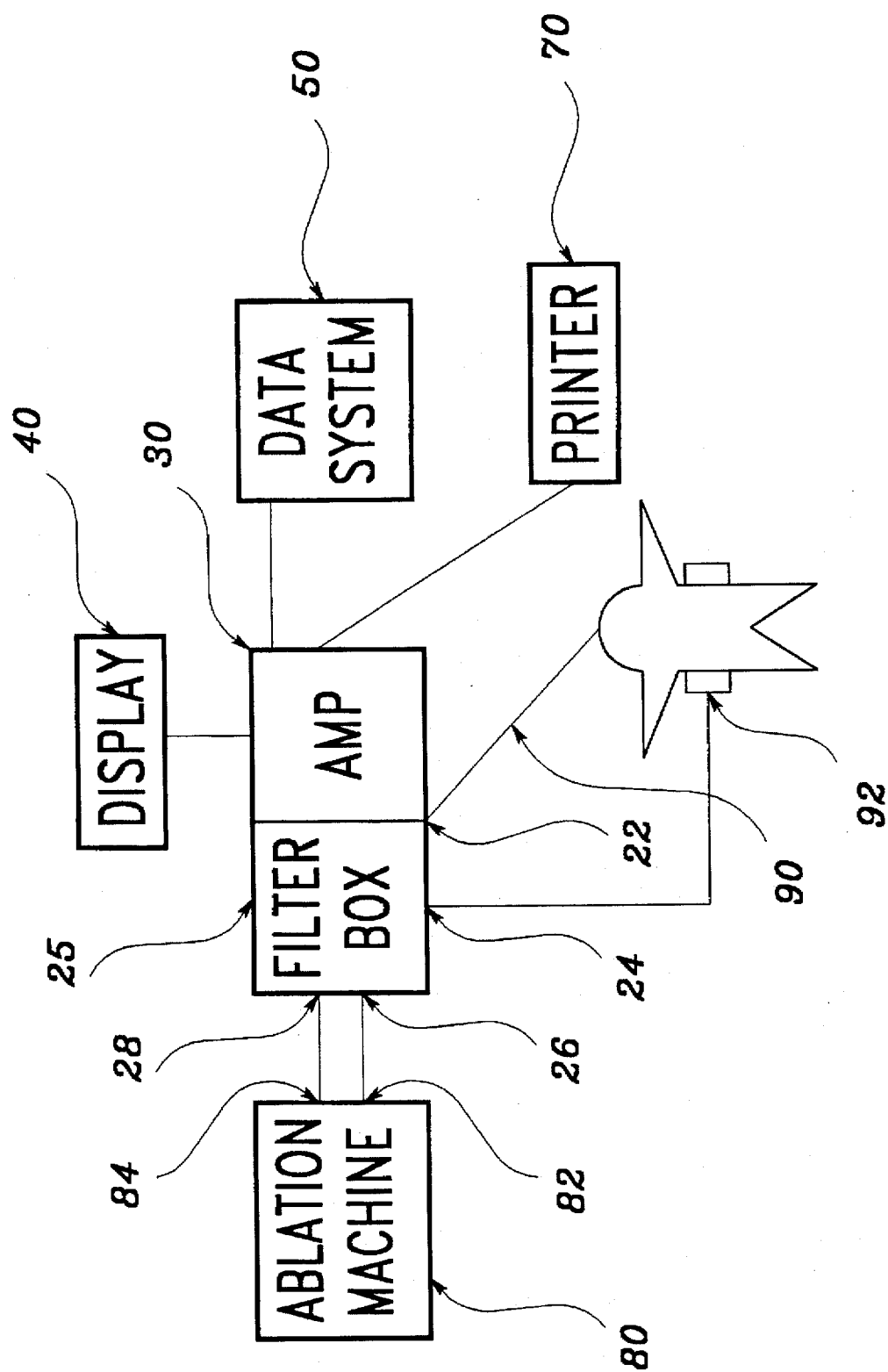
FIG. 3 is a diagrammatic view of an alternate embodiment of an electrophysiology system formed in accordance with the principles of the present invention.

In FIG. 1, the amplification system 30 is shown as being connected to a display monitor 40, a data management and analysis system 50 and a chart recorder or printer 70. The basic components of the electrophysiology system 10 include an ablation machine 80, the amplification system 30 and at least one of the monitor 40, data management and analysis system 50 and chart recorder or printer 70 in addition to the filter box 20 which may be separate from the remaining components or may be integral with the amplification system 20 to provide a modified filter box 25 as shown in FIG. 3.

As schematically shown in FIG. 2, the filter box 20 is preferably a single pole "T" type of passive filter. The capacitors 32 and 34 provide a very low impedance to the ablation energy signal. In the preferred form of the invention, the impedance provided by the capacitors is less than 1 ohm. An inductor 36 is also preferably provided to form a high impedance to the ground at the ablation frequencies. A resistor 38 is also preferably provided in the present invention. These components form a filter pole between about 5000 and 10000 Hz to block in the band noise which is received from the ablation machine 80 on the ablation side of the filter box 20.

In the present invention, when the physician is performing an electrophysiology study, the endocardial signals are received from the patient via the ablation catheter 90. The endocardial signals pass directly from the ablation catheter 90 to the amplification system 30 via a parallel connection. The noise generated by the ablation machine 80 is prevented from interfering with the endocardial signals by the filter pole which blocks the in band noise coming from the ablation machine 80 on the ablation machine side of the filter box 20 while also blocking the endocardial signal on the patient side of the filter box 20 to prevent the endocardial signal from being shorted out by the ablation machine. When the physician is performing an ablation procedure, the ablation energy is passed from the ablation machine 80, through the capacitors 32 and 34 and to the ablation electrode 90. Ideally, the amount of energy consumed by the filter pole is less than one percent of the ablation energy, although it is believed that a filter pole which consumes up to approximately ten percent of the ablation energy would not substantially affect the physicians ability to perform the ablation procedure.

The signal received from the ablating pole of the ablation catheter 90 contains both the ablation energy signal and the endocardial signal. The filter box 20 blocks the signal on the patient side of the filter box and prevents the signal from being shorted out by the ablation machine 80. The amplification system 30 separates the mixed signal received from the ablation catheter 90 by using a low pass filter in the range of 40 to 12,000. The resulting signal is representative of the endocardial signal which is received by the amplification system 30 from the patient throughout the entire electrophysiology study and the ablation procedure. The signal may be further processed or filtered by the amplification system 30 or the data management and analysis system 50 as needed.

FIG. 3 is illustrative of an alternate embodiment of the present invention wherein the filter box 20 described above is modified to be integral with the amplifying system 20. In this embodiment, filter in 52, filter out 54, and two ground terminals, 56 and 58 are located on the side or back of the amplification system 30 so that the ablation machine 80 and ablation catheter are easily connected to the modified filter box 25. In this embodiment, a shield (not shown) may be used between the components of the filter box 25 and the amplification system 30 to protect the amplification system 30 from excess noise or interference which may be caused by the ablation machine 80 or ablation catheter 90. As with the embodiment described, the filter box 25 also preferably includes a patient side and a machine side. An advantage of the present embodiment is that one less component or box is used and therefore, the overall electrophysiology system 10 will require less space and will be less intimidating to the user.

It will be apparent from the foregoing that, while particular embodiments of the invention have been illustrated and described, various modifications can be made thereto without departing from the spirit and scope of the invention. Accordingly, it is not intended that the invention be limited, except as by the appended claims.

What is claimed is:

1. An electrophysiology system for monitoring the physiological data of a patient from an electrophysiology study and performing an ablation procedure, the system comprising:
    an amplification system for receiving and amplifying endocardial data from a patient;
    an ablation machine for generating an energy signal to ablate portions of a heart in accordance with said endocardial data;
    an ablation catheter for delivery of the energy signal to the heart of the patient and to provide endocardial data from the heart of the patient to the amplification system; and
    a filter box interconnected with said amplification system, said ablation machine and said ablation catheter and having a filter array therein to filter said endocardial data for use by said amplification system while said energy signal is generated by said ablation machine and applied to the heart of a patient through said ablation catheter and while said energy signal is not applied to the heart of the patient.

2. The system of claim 1 wherein said amplification system includes a monitor associated therewith to provide a display of the physiological data received from the patient.

3. The system of claim 1 wherein said filter box includes a passive filter therein.

4. The system of claim 1 wherein said filter box includes a first filter member having an impedance less than about 1 ohm at approximately 500 kHz therein.

5. The system of claim 1 wherein said filter box includes a filter member having an impedance greater than about 3000 ohms at approximately 500 kHz therein.

6. The system of claim 1 wherein said filter box includes a patient side and an ablation machine side and said filter array results in a filter pole between about 5000 and 10000 ohms as measured from the patient side of said filter box.

7. The system of claim 1 wherein said filter array blocks the noise generated by said ablation machine which is generally within the same frequency range as the endocardial data from the patient.

8. The system of claim 1 wherein said amplification system includes further filters therein to filter the signal received by said amplification system from said filter box to provide a signal which is representative of the endocardial data received from the patient by said ablation catheter.

9. The system of claim 1 wherein said filter box includes a patient side and an ablation machine side and said filter box includes a first filter member having an impedance less than about 1 ohm at approximately 500 kHz and a second filter member having an impedance greater than about 3000 ohms at approximately 500 kHz and said filter array of said filter box has a filter pole between about 5000 and 10000 Hz as measured from said patient side of said filter box.

10. The system of claim 1 further including a chart recorder for printing the physiological data from the patient and a display system including a display monitor wherein said chart recorder and said display monitor are independently configurable through said amplification system.

11. The system of claim 1 further including a separate data management system operatively connected to said amplification system and a display system which includes a real time display monitor operatively associated therewith and the operation of said monitor and said data management system being in response to command signals received from said amplification system.

12. The system of claim 1 further including a separate chart recorder operatively connected thereto and a display system which includes a real time display monitor operatively associated therewith and the operation of said monitor and said chart recorder being in response to command signals received from said amplification system.

13. The system of claim 1 further including a passive filter in said filter box and at least one low pass filter in said amplification system.

14. The system of claim 1 including a single pole type of filter in said filter box and at least one low pass filter in said amplification system.

15. The system of claim 1 including said filter array which provides an impedance of less than 1 ohm at approximately 500 kHz to said energy signal generated by said ablation machine and which blocks in band noise generated by said ablation machine that is in the same frequency range as the endocardial data generated by the heart of the patient.

16. The system of claim 1 further including a filter member having a high impedance to ground at the frequencies at which said energy signal is generated by said ablation machine.

17. The system of claim 1 further including a plurality of filters in said amplification system wherein said plurality of filters include adjustable high and low pass and notch filters.

18. An electrophysiology system for monitoring the physiological data of a patient from an electrophysiology study and an ablation procedure, said system including an amplification system for amplifying the physiological signals received from the body of the patient, an ablation machine for generating a high energy ablation signal, an ablation catheter for delivering said ablation signal to a location inside the heart of a patient and receiving endocardial signals from the heart of the patient and a filter box operatively connected to said amplification system, said ablation machine and said ablation catheter, said filter box including:
    an interface means for interfacing with the endocardial signals received from said ablation catheter and supplying said endocardial signals to said amplification system, said interface means including filters therein and further receiving said ablation signal from said ablation machine and transferring said ablation signal to said ablation catheter while allowing said endocardial signals to be received by said amplification system during an electrophysiology study and an ablation procedure without modification thereof.

19. The system of claim 18 wherein said endocardial signals are received by said interface means and said amplification system in parallel.

20. The system of claim 18 wherein said interface means includes a single pole passive filter therein.

21. The system of claim 18 wherein said interface means includes a plurality of capacitors therein to provide an impedance of less than 1 ohm to said ablation signal therein.

22. The system of claim 18 wherein said interface means includes an inductor therein having an impedance greater than 3000 ohms to ground at the frequencies at which said ablation signal is generated by said ablation machine.

23. The system of claim 18 wherein said interface means includes an ablation machine side and said interface means includes a filter pole therein to block the in band noise from said ablation machine on said ablation machine side of said interface means.

24. The system of claim 18 wherein said interface means includes an amplification system side and said interface means includes a filter pole therein to block the endocardial signals from said ablation catheter on said amplification system side of said interface means and to allow said endocardial signals to be received by said amplification system.

25. A method of performing an electrophysiology study and ablation procedure using an electrophysiology system including an ablation machine, an ablation catheter, a filter box having a patient side and an ablation machine side and an amplification system to receive endocardial signals during the electrophysiology study and the ablation procedure, said method including passing an ablation signal generated by the ablation machine through the filter box and ablation catheter to the patient, blocking the in band noise generated by the ablation machine on the ablation machine side of the filter box while also blocking the endocardial signals on the patient side of the filter box, and processing the endocardial signals in the amplification system.

26. The method of claim 25 including the step of passing the ablation signal through a filter pole formed by the components of the filter box between about 5000 Hz and 10000 Hz to block the in band noise generated by the ablation machine.

27. The method of claim 25 including the step of passing the endocardial signals from the ablation catheter to the amplification system through a parallel connection.

28. The method of claim 25 including the step of filtering the endocardial signals in the amplification system using a low pass filter.

29. The method of claim 25 including the step of providing a passive filter in the filter box to provide a low impedance to the passage of the ablation signal therethrough.

30. The method of claim 25 wherein the ablation signal is an energy signal generated by the ablation machine and the method further includes the step of providing a passive filter in the filter box to provide an impedance to the passage of the ablation signal therethrough which is less than one percent of the energy generated by the ablation signal of the ablation machine.

31. The method of claim 25 including the step of passing the ablation signal through a filter member having an impedance greater than about 3000 ohms at approximately 500 kHz.

32. The method of claim 25 including the step of continuously processing the endocardial signals in the amplification system during the electrophysiology study and the ablation procedure.

* * * * *